United States Patent [19]

Corvi Mora

[11] Patent Number: 4,605,792
[45] Date of Patent: Aug. 12, 1986

[54] DERIVATIVE OF (−)-6,6-DIMETHYLBICYCLO[3.3.1]EPT-2-ENE-2-METHANOL HAVING MUCOSECRETOLYTIC ACTIVITY, A PROCESS FOR ITS PREPARATION AND PHARMACEUTICAL COMPOSITIONS THEREOF

[75] Inventor: Camillo Corvi Mora, Piacenza, Italy
[73] Assignee: Camillo Corvi S.p.A., Italy
[21] Appl. No.: 742,574
[22] Filed: Jun. 7, 1985
[30] Foreign Application Priority Data Aug. 8, 1984 [IT] Italy ............................... 22258 A/84

[51] Int. Cl.$^4$ ............................................. C07C 35/18
[52] U.S. Cl. .................................. 568/823; 568/715; 568/824
[58] Field of Search .................. 568/824, 823, 715

[56] References Cited

U.S. PATENT DOCUMENTS 2,883,398  4/1959  Frostixk et al. ..................... 568/823
2,949,489  8/1960  Durbetaki et al. .................. 568/823

FOREIGN PATENT DOCUMENTS 649603  10/1962  Canada ............................... 568/823

OTHER PUBLICATIONS

Ventura et al., "Chemical Abstracts" vol. 99 (1983) p. 115465s.
Baib, "J. Amer. Chem. Soc." vol. 68, pp. 638–642.
P. Ventura, M. Schiavi and S. Serafini, "The Metabolism of Trans–Sobrerol in the Rat", Xenobiotica, 1983, vol. 13, No. 3, pp. 139–146.

Primary Examiner—Werren B. Lone
Attorney, Agent, or Firm—Ostrolenk, Faber, Gerb & Soffen

[57] ABSTRACT

A novel derivative of (−)-6,6-dimethylbicyclo[3.3.-1]ept-2-ene-2-methanol is disclosed.

The compound which is an object of the present invention, is the derivative :α,α-dimethyl-5-hydroxy-3-cyclohexene-1,4-dimethanol.

The present invention further discloses the process for obtaining the compound which consists in preparing the (−)-6,6-dimethylbicyclo[3.3.1]ept-2-ene-2-methanol epoxide, thereafter hydrating the above compound and separating the compound from the hydration products. Finally, this invention comprises the pharmaceutical compositions containing the compound which possess a pharmacological mucosecretolytic activity.

3 Claims, No Drawings

DERIVATIVE OF (−)-6,6-DIMETHYLBICYCLO[3.3.1]EPT-2-ENE-2-METHANOL HAVING MUCOSECRETOLYTIC ACTIVITY, A PROCESS FOR ITS PREPARATION AND PHARMACEUTICAL COMPOSITIONS THEREOF

DESCRIPTION OF THE INVENTION

The subject of the present invention is the compound α,α-dimethyl-5-hydroxy-3-cyclohexene-1,4-dimethanol, having the structural formula

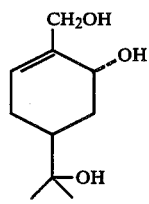

(I)

Code CO/1470
$C_{10}H_{18}O_3$ mol.wt. 186.24; m.p. 114°–116° C.

It has been found that (−)-6,6-dimethylbicyclo[3.3.1]ept-2-ene-methanol (also known as (−)myrtenol see 1981-1982 Aldrich-Europe Catalog Handbook of Fine Chemicals, No. 18.841-7) can form an epoxide by treatment with peracids such as m-chlorobenzoic acid or peracetic acid (40% acetic solution).

The epoxide is obtained when, in particular, peracetic acid is employed, in a medium of anhydrous methylene chloride (ethanol free), in the presence of anhydrous sodium carbonate which acts as an acid acceptor. In the reaction medium there forms, concurrently with the epoxidation, an equimolar salt mixture of anhydrous sodium bicarbonate and sodium acetate which can be eliminated by filtration or by water dissolution and separation of the chloromethylene solution of the formed epoxide. The organic chloromethylene solution as separated is then concentrated by evaporation under reduced pressure, to give the concentrated epoxide. The obtainment of the epoxide of (−)-6,6-dimethylbicyclo[3.3.1]ept-2-ene-2-methanol of formula (II) has led to make investigations on the hydration products, which may be obtained in an aqueous medium, in the presence of either diluted strong acids (1% solution of $H_2SO_4$, $H_3PO_4$) or weak acids (such as $H_2CO_3$, $H_2SO_3$) at temperatures from 1° to 20° C.

There is thus obtained the product of formula (I), which is the subject of the present invention.

The product of the formula (I) has shown a very interesting pharmacological activity as a mucolytic agent for bronchial secretion, which causes the product of formula (I) to constitute potentially a novel drug intended for the therapy of acute as well as chronic diseases of the broncho-pneumonic apparatus

SYNTHESIS SCHEME OF CO/1470

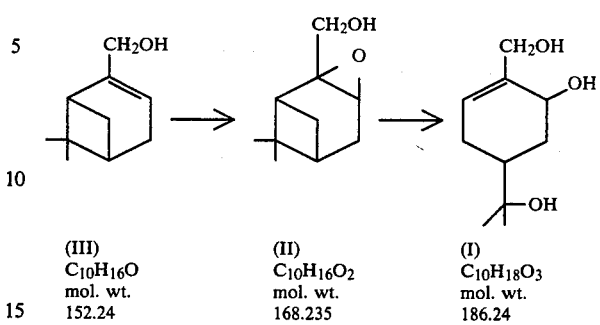

| (III) | (II) | (I) |
|---|---|---|
| $C_{10}H_{16}O$ | $C_{10}H_{16}O_2$ | $C_{10}H_{18}O_3$ |
| mol. wt. | mol. wt. | mol. wt. |
| 152.24 | 168.235 | 186.24 |

CO/1470

Elemental analysis: Calculated: C=64.49%, H=9.74%, O=25.77%; Found: C=64.37%, H=9.92%, C=64.40%, H=9.94%, C=64.35%, H=9.86%.

I.R. (nujol dispersion; cm$^{-1}$): 3290 νOH; 1140; 1057; 1025; 1011; 1005; 963; 930; 835; characteristic bands.

N.M.R. ($D_2O$ solvent; D.S.S. reference; δppm): 6.0 centre c.a.(1H; =CH), 4.33 centre c.a.(1H; CH—OH; $W_{\frac{1}{2}}=7.5$ $H_2$), 4.12 c.a.(2H; $CH_2$—OH), 2.43÷1.32 c.a.(5H; $CH_2$—CH—$CH_2$), 1.22 s. (6H; gem. $CH_3$).

c.a. = complex absorption
$W_{\frac{1}{2}}$ = broadness at half height
s. = singlet
D.S.S. = 3(trimethylsilyl) propane-sulfonic acid, sodium salt M.S.(Quadrupole; electronic impact, direct insertion, 80 eV, 70 mA, m/z): 168[(M-18)+, 1%]; 153[(M-18-15)+, 3%]; 151 (2%); 150 (10%); 137 (8%); 135 (13%); 126 (11%); 122 (4%); 114 (11%); 110 (10%); 109 (9%); 108 (17%); 107 (16%); 106 (5%); 105 (3%); 97 (5%); 96 (9%); 95 (41%); 94 (5%); 93 (12%); 92 (23%); 91 (22%); 82 (9%); 81 (27%); 80 (9%); 79 (44%); 78 (11%); 77 (15%); 69 (17%); 67 (16%); (base peak).

TABLE 1

Bronchosecretagogue activity of CO/1470

Below are reported the average values of percent increase of the bronchial mucus secretion upon treatment with CO/1470 and other known standards as compared to the basal values. Further, there is reported the number of rabbits which showed an increase of bronchial secretion as compared with all the animals treated with CO/1470 at the various doses and via the two administration routes as utilized (R. Scuri et al., Boll. Chem. Farm., 119, 181-7, 1980).

| Dose in mg/Kg | Administration way | Bronchial secretion average increase, % | N° of rabbits with a secretion increase/N° of rabbits CO-treated |
|---|---|---|---|
| CO/1470 | | | |
| 25 | oral | 42 | 3/10 |
| 100 | oral | 54 | 8/11 |
| 400 | oral | 171 | 10/10 |
| 2,5 | intravenous | 20 | 4/10 |
| 5 | intravenous | 59 | 7/10 |
| 10 | intravenous | 72 | 9/10 |
| N—acetylcysteine | | | |
| 400 | oral | 22 | 8/16 |
| 600 | oral | 59.4 | 6/9 |

| Dose in mg/Kg | Administration way | Bronchial secretion average increase, % | N° of rabbits with a secretion increase/N° of rabbits CO-treated |
|---|---|---|---|
| Bromhexine | | | |
| 200 | oral | 35.8 | 4/8 |
| 400 | oral | 43 | 6/8 |
| Carboxymethylcysteine | | | |
| 200 | oral | 10 | 4/10 |
| 400 | oral | 46 | 5/10 |

EXAMPLE

To a solution of 30 g (−)-6,6-dimethylbicyclo-[3.3.1]ept-2-ene-2-methanol in 300 ml methylene chloride, 34 g of anhydrous sodium carbonate are added. The resulting mixture is cooled to a temperature of 5° to 10° C. and 60 ml of 40% peracetic acid, under vigorous stirring, are added thereto. At the end of the addition, the cooling is interrupted and the mixture is left under stirring at room temperature over 12 hours. The reaction mixture is diluted with water, the organic phase is separated, washed with water, dessiccated and evaporated to dryness; 31.5 g (95%) of epoxide are so obtained. To the above compound, 60 ml of water and 10 g of solid carbon dioxide are added and the resulting mixture is stirred vigorously over 3 hours. It is diluted with water saturated with sodium chloride, and it is extracted repeatedly with ethyl acetate. The combined organic phases are washed with a little water, anhydrified and concentrated to a volume of about 100 ml. The precipitate is suction filtered and 14 g (38%) of a white crystalline product, m.p. 114°-116° C., are thus obtained. Referring to the activity as a mucosecretolytic agent shown by the compound of formula (I), the present invention further provides pharmaceutical compositions which contain the compound of formula (I) in dosage unit.

The pharmaceutical forms containing the above mentioned active ingredient are those for intramuscular and intravenous administration and those for aerosol, as well as the ones for oral administration, in particular: capsules, tablets, granular forms in sachets, syrups and forms for rectal administration (suppositories).

In the forms as mentioned, conventional excipients are combined with the compound of formula (I).

In the solid oral forms (tablets, capsules, granular forms), the preferred excipients are: lactose, starch, cellulose and its derivatives, with all the carrier materials for the preparation of the pharmaceutical form such as precipitated silica, talc, calcium or magnesium stearate.

In the form of syrup, the active compound is dissolved in a sugar solution (saccharose, glucose, sorbitol) with addition of aromatizing and preserving agents.

In the form of suppositories, the main excipient consists of triglycerides of fatty acids, either pure or as a mixture with oxyethylated derivatives.

In the injectable or aerosol forms, the compound of formula (I) is brought to an isotonic solution and either cold or hot sterilized.

I claim:

1. A process for the preparation of a compound of formula (I)

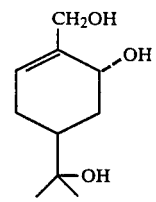

characterized by the epoxidation of (−)-6,6-dimethylbicyclo[3.3.1]ept-2-ene-methanol in an anhydrous methylene chloride medium free from ethanol at a temperature of 5° to 10° C. in the presence of anhydrous sodium carbonate, by peracetic acid in a 40% acetic solution; the pure epoxide, as obtained upon separation from the salts, is subjected to hydration at a temperature from 1° to 20° C. in an weakly acid aqueous medium, extracted with ethyl acetate in the presence of a sodium chloride solution, and concentration of the organic phase, whereby the compound of formula (I), in crystalline form, is obtained.

2. Pharmaceutical composition having mucosecretolytic activity, comprising a compound of formula (I)

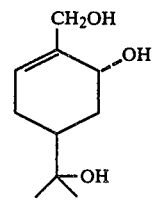

pharmaceutically acceptable carrier.

3. A method of increasing mucosecretolytic activity which comprises administering to a host an effective mucosecretolytic amount of a compound of formula (II)

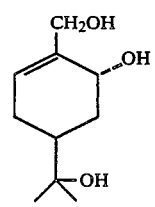

* * * * *